United States Patent [19]

Shields et al.

[11] Patent Number: 4,993,432

[45] Date of Patent: Feb. 19, 1991

[54] APPLICATOR FOR CERVICAL CAPS

[76] Inventors: Jack W. Shields, 1950 Las Tunas Rd., Santa Barbara, Calif. 93103; Richard P. Jobe, 26965 Orchard Hill La., Los Altos Hills, Calif. 94022

[21] Appl. No.: 329,937

[22] Filed: Mar. 28, 1989

[51] Int. Cl.[5] .................................................. A61F 6/06

[52] U.S. Cl. .................................... 128/838; 606/107; 606/119; 294/1.2

[58] Field of Search ............... 128/832, 834, 835, 836, 128/837, 839, 840, 841, 303 R, 838; 623/2; 239/3; 606/107, 162, 119–126; 294/1.2

[56] References Cited

U.S. PATENT DOCUMENTS

| | | | |
|---|---|---|---|
| 3,129,971 | 4/1964 | Kobler | 294/1.2 |
| 3,346,187 | 10/1967 | Mueller | 239/33 |
| 4,093,291 | 6/1978 | Schurgin | 294/1.2 |
| 4,372,302 | 2/1983 | Akerlund | 128/840 |

*Primary Examiner*—Robert A. Hafer
*Assistant Examiner*—Lynda M. Cofsky
*Attorney, Agent, or Firm*—Michael G. Petit

[57] ABSTRACT

An applicator device for insertion and removal of a cervical cap is described. The device utilizes manually controlled suction to grip the cervical cap during placement and a retrieval hook to facilitate removal.

4 Claims, 1 Drawing Sheet

13 10 11 16 15 14

APPLICATOR FOR CERVICAL CAPS

FIELD OF THE INVENTION

The invention relates to an applicator for gripping and manipulating a cervical cap or similar contraceptive device.

BACKGROUND ART

Although the use of cervical caps as a contraceptive device has been know for many years (see for example U.S. Pat. No. 2,020,107 to Cruickshank, issued Nov. 5, 1935), they have not been widely accepted or enjoyed commercial success until the last year or two. The recent interest in cervical caps is due, in part, to the rapidly increasing risk of contracting AIDS or other sexually transmitted diseases during sexual intercourse.

It is now known that the most probable place for the AIDS virus (HIV) to enter a female upon contact with infected semen is in the vicinity of the external os of the cervix uteri. Migrant lymphocytes present in the infected semen carry the AIDS virus. Only in the endocervix is the epithelium thin enough to permit passage of an infected lymphocyte. A barrier device that protects the endocervix from contact with such infected lymphocytes is, therefore, not only an effective contraceptive device but a defense against the lymphocyte transmitted AIDS virus.

Cervical caps comprise a pre-formed rubber cap that is positioned over the cervix uteri to act as a sperm barrier. Such caps are manufactured in several sizes to accommodate the various uterine sizes normally encountered. Recently, Loeb (U.S. Pat. No. 4,320,751) described a cervical cap with a foam liner wherein a single size can adjust to fit snugly against the cervix uteri for a range of uterine sizes. This type of cap is generally a dome-like flexible shell having a convex outer surface and a soft resilient form-assuming inner liner.

Although cervical caps are a safe and effective alternative to diaphragms, they are more difficult to position and remove. It is an object of this invention to provide a personal applicator to facilitate insertion and removal of such cervical caps. It is yet another object of this invention to provide an applicator that can be adjusted to accommodate individual variation in the angle of presentation of the cervix uteri with respect to the vaginal canal.

SUMMARY OF THE INVENTION

The foregoing objectives are realized by providing an applicator which enables the user to grip the cervical cap firmly by suction during insertion and/or removal. The applicator comprises a ring shaped concave applicator tip contoured or beveled on its inner surface to mate with a portion of the normally convex exterior surface of a cervical cap. The cervical cap is inserted into the applicator tip and held in position by vacuum suction. The vacuum is generated by manually pumping the air out of a central cavity in the applicator handle. Once the cervical cap is positioned properly over the cervix uteri, the vacuum is released by squeezing the handle a second time thereby releasing the cervical cap and the applicator is withdrawn. For removal, the process is reversed except that a hook on the periphery of the applicator tip mechanically dislodges the cervical cap from the cervix uteri by breaking the surface tension created by the presence of a film of mucous and cervical fluids between the cervical cap and cervix uteri.

While the applicator device described herein could be made in a variety of angles suited to a particular user, the present invention also contemplates an applicator having a adjustable handle portion to enable a user to introduce a cervical cap into the vagina at the appropriate angle.

DETAILED DESCRIPTION OF THE INVENTION

Figure 1:
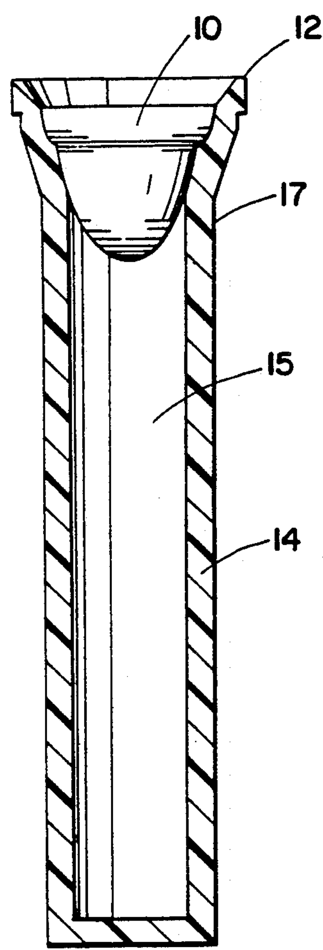
FIG. 1 is a cross-sectional side view of a first preferred embodiment of the present invention.

Referring now to FIG. 1, a first preferred embodiment of the invention is described. The applicator device consists of a handle (14) made of silicone tubing with an outside diameter of 32 mm and an inside diameter of 22 mm which is convenient for use with a 25 mm cervical cap. The internal diameter of the tube may be selected to accommodate to the diameter of the cervical cap it is intended to be used with which may range from 22–31 mm. The upper end of the handle, or applicator end, (17) terminates in a cup-shaped applicator tip (12) which is molded to accommodate and mate with a portion of the outer surface of a cervical cap (10). When the cervical cap (10) is pressed into the mating applicator tip (12) (which applicator tip may be lined with closed cell silicone foam to provide a snug fit for a variety of sizes of cervical caps), the handle (14) is gently squeezed thereby forcing air out of the cavity (15). While squeezing the handle a cervical cap (10) is pressed into the mating applicator tip (12) to effectively seal the cavity (15). When the squeezing pressure on the outer wall of the handle (14) is released, a partial vacuum forms in the cavity due to the restoring forces in the deformed silicone wall (14) of the cavity thus holding the cervical cap firmly in the applicator tip. The applicator is then grasped by the handle and used to introduce the cervical cap onto the cervix uteri. Once the cervical cap is correctly positioned on the cervix uteri, the handle is squeezed to release the partial vacuum in the cavity (15) and the applicator is removed. Surface tension between the cervical mucous and the interior surface of the cervical cap will secure the cap to the cervix uteri. For removal of the cervical cap, a removal ring (FIG. 2(11)) is slipped over the handle and securely snapped over the applicator tip (12). The removal ring has a removal hook (13) (FIG. 2) which, when hooked over the marginal flange of a cervical cap, breaks the surface tension between the film of mucous and fluid coating the cervix and the inner surface of the cervical cap thereby dislodging the cap and enabling the cervical cap to be removed with the fingers.

Figure 2:
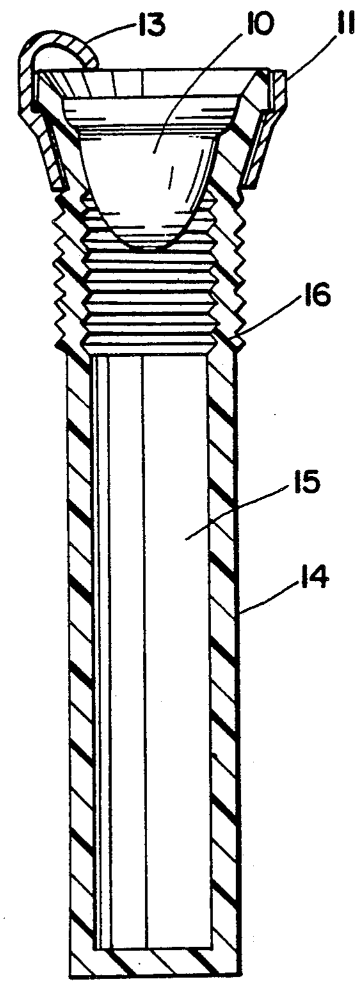
FIG. 2 is a cross sectional side view of a second preferred embodiment of the present invention.
Figure 3:
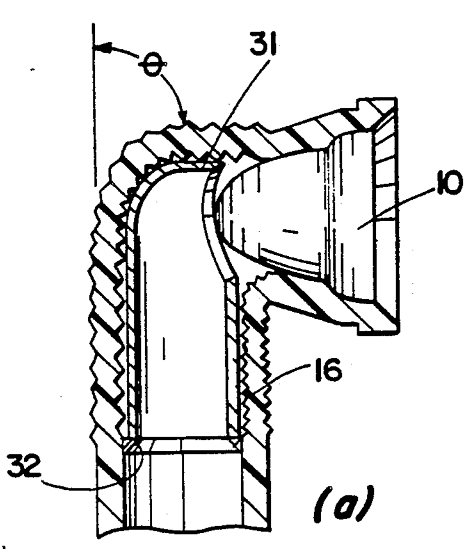
FIG. 3 is a cross-sectional side view of the suction tip portion of FIG. 1 (FIG. 3(*a*)) and FIG. 2 (FIG. 3(*b*)) wherein the suction tip is bent at an angle to the axis of the applicator handle.
Figure 3:
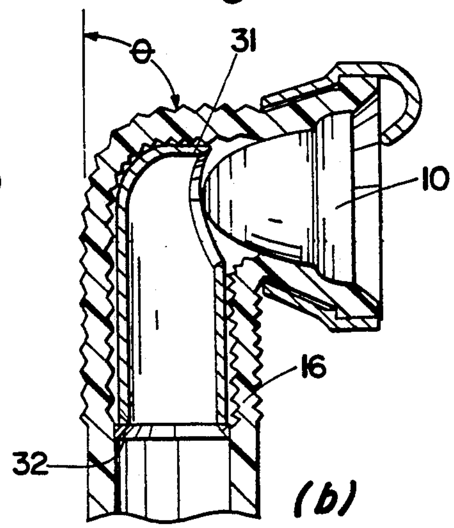

FIG. 2 shows an embodiment similar to FIG. 1 except that the applicator handle (14) is of a rigidly flexible elastomeric material as in FIG. 1 but molded with an accordion-fold (16) at the applicator end (17) of the handle (14). The accordion-fold facilitates bending of the applicator end of the handle to vary the angle ($\theta$)

between the axis of the applicator tip and the axis of the handle as shown in FIG. 3(*a*) (without the retrieval ring and FIG. 3(*b*) with the retrieval ring). A malleable metal strip (31) is insertion molded into the handle near the suction tip to facilitate adjustment of the angle. Alternatively, a removable malleable sleeve may be slipped into the handle. The removable sleeve is prevented from moving by a ridge or detent (32) on the interior portion of the handle (14). The accordion fold prevents the suction tip end of the handle from kinking when the tip is bent to facilitate insertion of the cervical cap at the proper angle.

In yet a further embodiment (not shown) a variable tensioning element such as string connects one side of the applicator tip with the handle. Tensioning the string bends the tip thereby varying the angle between the applicator tip and the handle. In addition, a manually operable value may be inserted into the handle to facilitate pressure regulation within the handle of the device.

The foregoing embodiments are presented by means of example and are not intended to limit the scope of the invention. The scope of this invention is more particularly set forth in the appended claims.

What we claim is:

1. An adjustable cervical cap applicator device for use with a cervical cap positioning said cervical cap over the cervix uteri, said cervical cap having an outer wall, at least a portion of which outer wall is substantially convex, said adjustable applicator comprising:

(a) an applicator tip portion, said tip portion being substantially annular and concave on its inner surface to permit a mating engagement with the outer surface of said cervical cap; and (b) an applicator handle portion, said handle portion housing a cavity therewithin and having an applicator end, said applicator end of said handle portion affixed to and terminating in said applicator tip portion, and a closed end;

(c) means for regulating the air pressure within said cavity when said cervical cap is matingly positioned within said applicator tip thereby loosely sealing said cavity, and (d) a malleable member positioned within said handle said malleable member permitting inclusive subtantially permanent adjustment of the angle between the axis of said applicator tip and the axis of said handle.

2. The adjustable cervical cap applicator device of claim 1 wherein at least a portion of said applicator handle portion is made of an elastomer dynamically responsive to manual pressure.

3. The adjustable cervical applicator device of claim 2 further comprising a cervical cap retrieval hook.

4. The applicator device of claim 1 further comprising a malleable material disposed within said handle portion to enable the angle between the axis of said applicator tip and the axis of the handle to be adjusted to a substantially permanent desired angle.

* * * * *